United States Patent
Fujimori (10) Patent No.: US 10,307,052 B2
(45) Date of Patent: Jun. 4, 2019

(54) OPHTHALMOLOGIC APPARATUS, METHOD OF CONTROLLING OPHTHALMOLOGIC APPARATUS, AND PROGRAM

(71) Applicant: CANON KABUSHIKI KAISHA, Tokyo (JP)

(72) Inventor: Toshiya Fujimori, Fujiidera (JP)

(73) Assignee: Canon Kabushiki Kaisha, Tokyo (JP)

( * ) Notice: Subject to any disclaimer, the term of this patent is extended or adjusted under 35 U.S.C. 154(b) by 24 days.

(21) Appl. No.: 15/422,622

(22) Filed: Feb. 2, 2017

(65) Prior Publication Data

US 2017/0231489 A1 Aug. 17, 2017

(30) Foreign Application Priority Data

Feb. 17, 2016 (JP) .................. 2016-027769
Nov. 30, 2016 (JP) .................. 2016-232938

(51) Int. Cl.
| | |
|---|---|
| *A61B 3/10* | (2006.01) |
| *G02B 26/10* | (2006.01) |
| *A61B 3/15* | (2006.01) |
| *A61B 3/00* | (2006.01) |
| *A61B 3/12* | (2006.01) |

(52) U.S. Cl.
CPC .......... *A61B 3/1025* (2013.01); *A61B 3/0025* (2013.01); *A61B 3/0091* (2013.01); *A61B 3/102* (2013.01); *A61B 3/1225* (2013.01); *A61B 3/156* (2013.01); *A61B 3/0033* (2013.01)

(58) Field of Classification Search
CPC ..... A61B 3/1025; A61B 3/0025; A61B 3/102; A61B 3/1225; A61B 3/156; A61B 3/0091; A61B 3/0033; G02B 26/101
See application file for complete search history.

(56) References Cited

U.S. PATENT DOCUMENTS

| | | |
|---|---|---|
| 2012/0154747 A1 | 6/2012 | Makihira |
| 2013/0188129 A1 | 7/2013 | Inoue |
| 2013/0215386 A1 | 8/2013 | Utagawa et al. |
| 2014/0118686 A1 | 5/2014 | Fujimori et al. |
| 2014/0132929 A1 | 5/2014 | Fujimori |
| 2014/0347631 A1 | 11/2014 | Kishida et al. |

FOREIGN PATENT DOCUMENTS

JP 2012-125490 A 7/2012

*Primary Examiner* — Jack Dinh
(74) *Attorney, Agent, or Firm* — Venable LLP (57) ABSTRACT

Provided is an ophthalmologic apparatus, including: a scan unit configured to repeat two-dimensional scanning on a fundus of an eye to be inspected with measuring light; an image generation unit configured to generate a two-dimensional image of the fundus based on reflected light of the measuring light from the fundus that is two-dimensionally scanned; and a control unit configured to control, in the two-dimensional scanning, an amount of the measuring light that is radiated to the fundus and is not used to generate the two-dimensional image to be smaller than an amount of the measuring light that is radiated to the fundus and is used to generate the two-dimensional image.

20 Claims, 9 Drawing Sheets

OPHTHALMOLOGIC APPARATUS, METHOD OF CONTROLLING OPHTHALMOLOGIC APPARATUS, AND PROGRAM

BACKGROUND OF THE INVENTION

Field of the Invention

The present invention relates to an ophthalmologic apparatus, which is configured to acquire an image of an eye to be inspected, a method of controlling the ophthalmologic apparatus, and a program for causing a computer to execute the method of controlling the ophthalmologic apparatus.

Description of the Related Art

At present, various ophthalmologic image acquiring apparatus are used, which are configured to scan an eye to be inspected with measuring light to observe the eye to be inspected and acquire an image thereof using the measuring light that is reflected by the eye to be inspected. Exemplary ophthalmologic apparatus include an optical coherence tomography (OCT) apparatus (hereinafter referred to as "OCT apparatus"), a scanning laser ophthalmoscope (SLO, hereinafter referred to as "SLO apparatus"), and an adaptive optics scanning laser ophthalmoscope (AO-SLO, hereinafter referred to as "AO-SLO apparatus"). In those apparatus, a galvano scanner, a resonant scanner, a polygon scanner, or the like is used to scan an eye to be inspected with measuring light so that data at a plurality of points of the eye to be inspected are continuously acquired.

In those apparatus, while scanning is performed with the measuring light to acquire one image, for example, it is preferred that a line of sight of the eye to be inspected be in a state of gazing in a certain direction. Here, in Japanese Patent Application Laid-Open No. 2012-125490, there is disclosed a fundus image acquiring apparatus (SLO apparatus), which is configured to project a fixation lamp on an eye to be inspected in order to prompt fixation of the eye to be inspected in scanning with the measuring light. In the fundus image acquiring apparatus, so-called raster scanning is performed. In the raster scanning, reciprocating scanning is performed once with the measuring light in a horizontal direction of a fundus image, and then a scanning position is shifted in a vertical direction to perform scanning again in the horizontal direction. After the raster scanning for one fundus image is finished, a position irradiated with the measuring light is returned to a start position of scanning with the measuring light in acquiring one fundus image, and the scanning with the measuring light for acquiring the next fundus image is repeated.

SUMMARY OF THE INVENTION

In order to solve the above-mentioned problem, according to one embodiment of the present invention, there is provided an ophthalmologic apparatus, including:

a scan unit configured to repeat two-dimensional scanning on a fundus of an eye to be inspected with measuring light;

an image generation unit configured to generate a two-dimensional image of the fundus based on reflected light of the measuring light from the fundus that is two-dimensionally scanned; and a control unit configured to control, in the two-dimensional scanning, an amount of the measuring light that is radiated to the fundus and is not used to generate the two-dimensional image to be smaller than an amount of the measuring light that is radiated to the fundus and is used to generate the two-dimensional image.

Further features of the present invention will become apparent from the following description of exemplary embodiments with reference to the attached drawings.

DESCRIPTION OF THE EMBODIMENTS

In the related art, in a series of movements of measuring light in moving an irradiation position from a scan end position of the measuring light after acquisition of one image is finished to a scan start position of the measuring light for acquiring the next image, the same eye to be inspected is always irradiated with the measuring light. Therefore, the movement of the position irradiated with the measuring light from the scan end position to the scan start position is seen from a subject to be inspected. The movement of the irradiation position presents a bright spot that traverses a field of view of the subject to be inspected, and leads to unstableness of fixation of the eye to be inspected.

In view of the above-mentioned circumstances, it is an object of an exemplary embodiment of the present invention to obtain a stable fixation state of an eye to be inspected in scanning with measuring light to acquire an image of the eye to be inspected.

Now, exemplary embodiments of the present invention are described with reference to the drawings. The following embodiments are not intended to limit the present invention defined in the appended claims, and not all combinations of features described in the following embodiments are essential to solving means of the present invention.

Further, in the following embodiments, a scanning laser ophthalmoscope (SLO apparatus) is given as an example of an ophthalmologic image acquiring apparatus. However, the present invention is not limited to only being applied to an SLO apparatus, and is generally applicable to ophthalmologic image acquiring apparatus configured to scan an eye to be inspected with measuring light, such as an OCT apparatus and an AO-SLO apparatus.

First Embodiment

An SLO apparatus according to a first embodiment of the present invention is described below with reference to the drawings.

(Schematic Structure of Apparatus)

Figure 1:
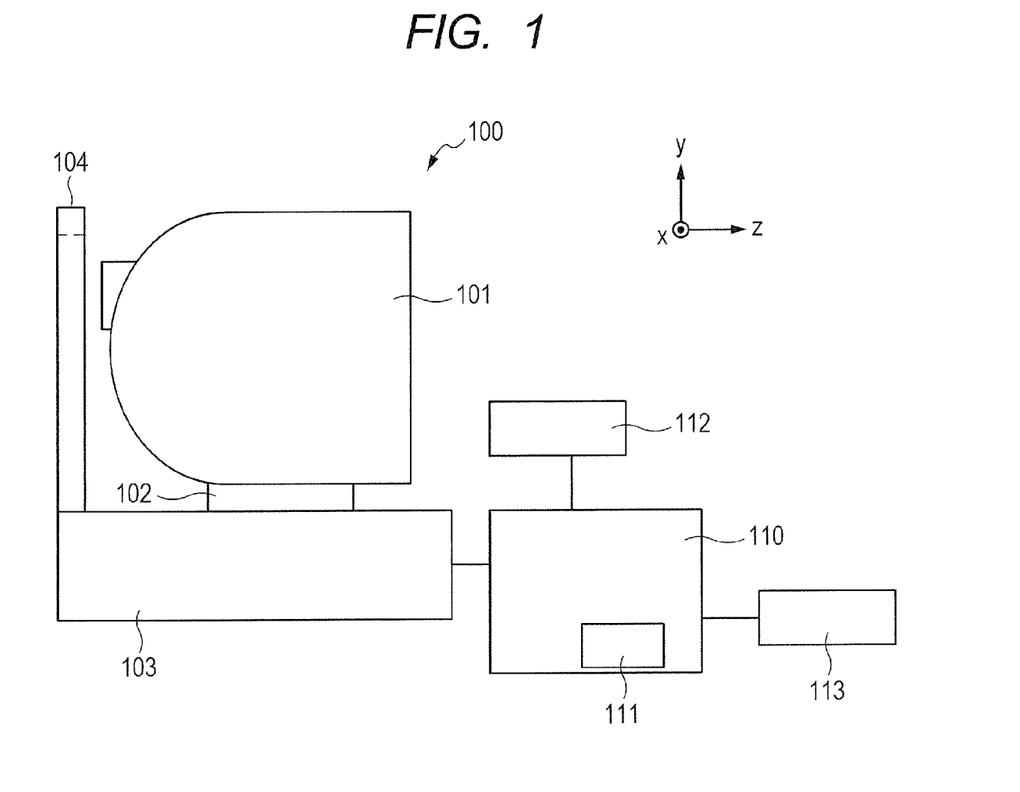
FIG. 1 is a schematic view for illustrating the structure of an entire ophthalmologic apparatus according to a first embodiment of the present invention.

FIG. 1 is an illustration of the schematic structure of the SLO apparatus according to this embodiment.

An SLO apparatus 100 illustrated in FIG. 1 includes an optical head 101, a stage portion 102, a base portion 103, a chin rest 104, a control portion 110, a storage portion 111, a display portion 112, and an input portion 113.

The optical head 101 houses therein an image acquiring optical system configured to acquire a two-dimensional image of a fundus portion of an eye to be inspected. The stage portion 102 includes a motor (not shown) or the like, and is configured to function as a drive portion capable of driving the optical head 101 in x, y, and z directions in FIG. 1 using the motor. The base portion 103 is configured to support the stage portion 102, and houses therein a power supply such as the motor, and part of the above-mentioned optical system and the like. The chin rest 104 is fixed to the base portion 103 and promotes fixation of an eye of a subject to be inspected (eye to be inspected) through fixation of the chin and the forehead of the subject to be inspected.

The control portion 110 is a personal computer that also serves as a control portion of the SLO apparatus 100, and is configured to control the SLO apparatus 100 and perform processing including construction of a fundus image. The storage portion 111 includes, for example, a hard disk configured to store therein a program for acquiring a fundus image, and is built into the control portion 110. The display portion 112 is a monitor configured to display a fundus image and the like. The input portion 113 includes, specifically, a keyboard and a mouse and is used for, for example, performing an operation of input to the control portion 110. In this embodiment, the control portion (personal computer), the hard disk, the display portion, and the input portion are provided outside the SLO apparatus 100. However, according to another aspect of the present invention, those components may be built into the SLO apparatus 100.

(Structure of Image Acquiring Optical System)

The structure of an image acquiring optical system of the SLO apparatus 100 according to this embodiment is described with reference to FIG. 2.

First, the structure inside of the optical head 101 is described. In the optical head 101, an objective lens 201-1 is arranged so as to be opposed to an eye 200 to be inspected. A first dichroic mirror 205 is arranged on an optical axis of the objective lens 201-1. An optical path leading to the eye 200 to be inspected is split by the first dichroic mirror 205 into an optical path L1 of an anterior ocular segment observing system and an optical path L2 of an internal fixation lamp and an SLO optical system, depending on the respective wavelength bands thereof.

On an optical axis of the optical path L1, a lens 204 and a lens 203 are arranged. With the lens 204 and the lens 203, light reflected from the anterior ocular segment of the eye to be inspected is received by a CCD 202 for observing an anterior ocular segment. The CCD 202 has sensitivity to a wavelength of illumination light for observing an anterior ocular segment (not shown), specifically, to a wavelength of approximately 970 nm.

A second dichroic mirror 209 is arranged on an optical axis of the optical path L2. The optical path L2 of light reflected from the fundus of the eye 200 to be inspected is split by the second dichroic mirror 209 into an optical path L3 of the internal fixation lamp optical system and an optical path L4 of the SLO optical system. A lens 201-2, a resonant scanner 206, a galvano scanner 207, and a lens 208 are arranged on the optical path L2 from the first dichroic mirror 205 side in this order, and the optical path L2 leads to the second dichroic mirror 209.

An SLO focus lens 210, a perforated mirror 211, an SLO light source 212, and a photodetector 213 are arranged on an optical axis of the SLO optical system (optical path L4) in a transmitting direction of the second dichroic mirror 209. The SLO focus lens 210 is driven in an optical axis direction, which is indicated by the arrow in FIG. 2, by a lens driving motor (not shown). The photodetector 213 forms a light receiving unit configured to receive a light beam that is projected onto the eye 200 to be inspected and is reflected from the eye 200 to be inspected in this embodiment. Further, a fixation focus lens 214 and an internal fixation lamp 215 are arranged on an optical axis of the internal fixation lamp optical system (optical path L3) in a reflecting direction of the second dichroic mirror 209. The fixation focus lens 214 is driven in the optical axis direction, which is indicated by the arrow in FIG. 2, by a lens driving motor (not shown).

The SLO light source 212 emits measuring light having a center value near a wavelength of 780 nm. Therefore, the photodetector 213 has sensitivity to light having a wavelength of approximately 780 nm to receive reflected light corresponding to the measuring light. Meanwhile, the internal fixation lamp 215 emits visible light to provide a fixation lamp to the eye to be inspected, and prompts the subject to be inspected to gaze at the fixation lamp to promote fixation of the subject to be inspected.

Each of the measuring light emitted from the SLO light source 212 and the fixation light emitted from the internal fixation lamp 215 forms an image once in the vicinity of the first dichroic mirror 205, and forms an image again in the vicinity of the fundus of the eye 200 to be inspected. The SLO focus lens 210 and the fixation focus lens 214 are driven on the optical axis by a lens driving motor (not shown) so that the positions of the images formed in the second formation match with a plane of the fundus of the eye 200 to be inspected. Through drive of those focus lenses, the positions of the images formed in the first formation also change in the vicinity of the first dichroic mirror 205.

The position of an image formed of the measuring light from the SLO light source 212 and the fixation light on the fundus is changed by the resonant scanner 206 configured to drive the measuring light in the X direction and the galvano scanner 207 configured to drive the measuring light in the Y direction. The scanners two-dimensionally scan the fundus with the measuring light and the fixation light. The measuring light scatters on the fundus. Reflected light scattered in a direction of the optical path L2 is reflected by the perforated mirror 211 to be detected by the photodetector 213. Through processing of a signal acquired by the photodetector 213 by a method to be described below, an SLO image is acquired. The fixation light is presented to the eye to be inspected as an indication fixed on the field of view to prompt the fixation of the eye to be inspected through turn-on control of the internal fixation lamp 215, for example. A position irradiated with the measuring light by the scanners, a region on the fundus scanned by the scanners, and the like are specified. In this way, the SLO apparatus 100 may acquire an image of an entire region of interest in a fundus portion of the eye 200 to be inspected.

The structure from the eye 200 to be inspected to the SLO optical system and the SLO optical system described above are merely exemplary, and are not limited to the structure of this embodiment. A scan unit configured to perform two-dimensional scanning on the region including the fundus or the fundus of the eye 200 to be inspected is configured to repeatedly perform the two-dimensional scanning on the region as described later. Further, the resonant scanner 206 and the galvano scanner 207 are included in the scan unit in this embodiment and are configured to actually scan the fundus with the measuring light. Each of the resonant scanner 206 and the galvano scanner 207 is configured to cause a mirror, which is configured to reflect the measuring light, to rotate in a predetermined angle range, to thereby deflect the reflecting direction of the measuring light and hence perform scanning with the measuring light. A direction of reciprocating scanning with the measuring light using the resonant scanner 206 is referred to as an "X direction" (first direction) for convenience, and a direction of reciprocating scanning with the measuring light using the galvano scanner 207 is referred to as a "Y direction" (second direction different from or perpendicular to the first direction) for convenience. A scanning speed of the resonant scanner 206 is higher than a scanning speed of the galvano scanner 207. Further, in general, with the resonant scanner 206 having a high scanning speed, it is difficult to correct the position irradiated with the measuring light as appropriate, for example. Therefore, instead of the galvano scanner 207, a scanner capable of correcting the position irradiated with the measuring light not only in at least the Y direction, which is the original scanning direction, but also in a direction other than the Y direction, and preferably in the X direction may be used. In other words, in this embodiment, the resonant scanner 206 is used as the X scanner, which performs scanning with the measuring light in the X direction, and the galvano scanner 207 is used as the Y scanner, which performs scanning in the Y direction, but scanners of other types may be used instead. Stated differently, the present invention is not limited to the structure described above as long as a scanning system is capable of performing scanning with the measuring light in the X direction at high speed, and of performing scanning with the measuring light in the Y direction at low speed.

Further, as described above, through the turn-on control of the internal fixation lamp 215 in synchronization with scanning with the resonant scanner 206 and the galvano scanner 207, various patterns such as a cross-shaped pattern or an X-shaped pattern can be projected onto various positions of the fundus of the eye to be inspected. With the internal fixation lamp 215 being configured as described above, the eye to be inspected may be directed to various directions. Therefore, control of the position at which the fixation target is presented and control of the scanning position of the measuring light may be combined to acquire an image of a wide region in the fundus portion of the eye 200 to be inspected.

Figure 2:
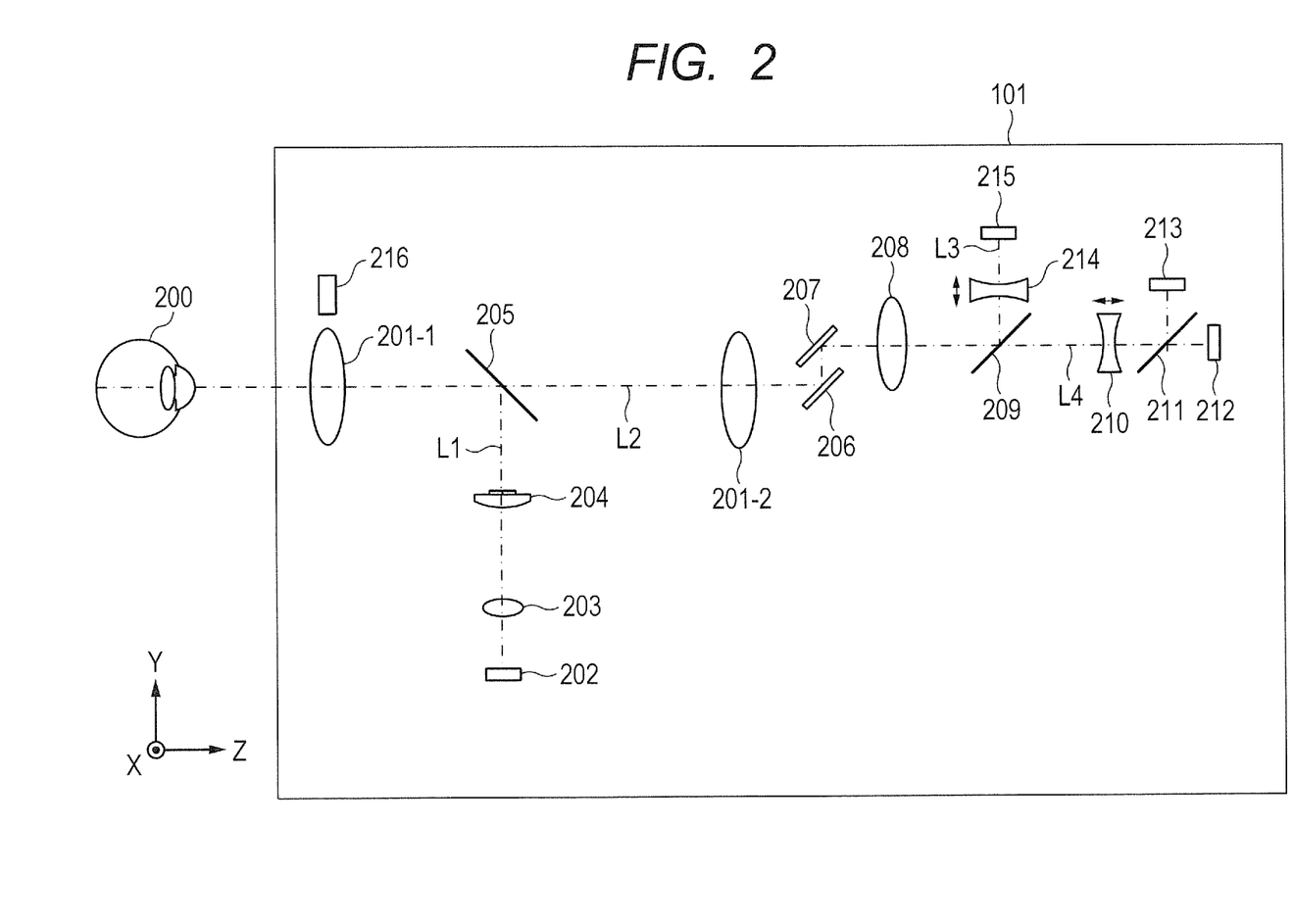
FIG. 2 is an explanatory view of an optical system in the ophthalmologic apparatus illustrated in FIG. 1.

In FIG. 2, an SLO image correcting photodetector 216 is arranged in the vicinity of the objective lens 201-1 at a position that deviates from the optical axis of the optical path L2 in the SLO apparatus 100. The SLO image correcting photodetector 216 is used as a photodetector for correcting the SLO image in a second embodiment of the present invention, which is to be described later.

(Generation of SLO Image)

Next, the SLO image acquired using the SLO apparatus 100 described above is described with reference to FIG. 3A and FIG. 3B.

Figure 3A:
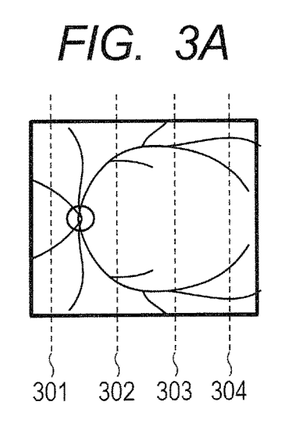
FIG. 3A and FIG. 3B are a diagram for illustrating an SLO image acquired by the ophthalmologic apparatus, and a graph for showing operation of a resonant scanner, respectively.

The control portion 110 is configured to convert a signal level acquired by the photodetector 213 to a brightness value of each pixel to generate an SLO image based on the brightness value. The actual SLO image is generated by a module configured to function as an image generating unit in the control portion 110. Specifically, the galvano scanner 207 drives the light beam on the fundus in the Y direction by an amount instructed by the control portion 110, and pixels acquired while the resonant scanner 206 scans the fundus once with the light beam in the X direction are arranged in a horizontal direction to acquire one-line data. Pieces of one-line data acquired by repeating the acquisition are arranged in a vertical direction (Y direction) to acquire a two-dimensional image as illustrated in FIG. 3A. The control portion 110 and the photodetector 213 form an image generating unit configured to generate a two-dimensional image of a predetermined region of the fundus based on the measuring light with which the two-dimensional scanning is performed.

The resonant scanner 206 is a scanner configured to perform reciprocating scanning, and thus, scanning at odd-numbered times and scanning at even-numbered times are performed in opposite directions. Therefore, in reality, data in odd-numbered lines and data in even-numbered lines are arranged in opposite directions such that a two-dimensional image with a unified direction is acquired as illustrated in FIG. 3A.

Figure 3B:
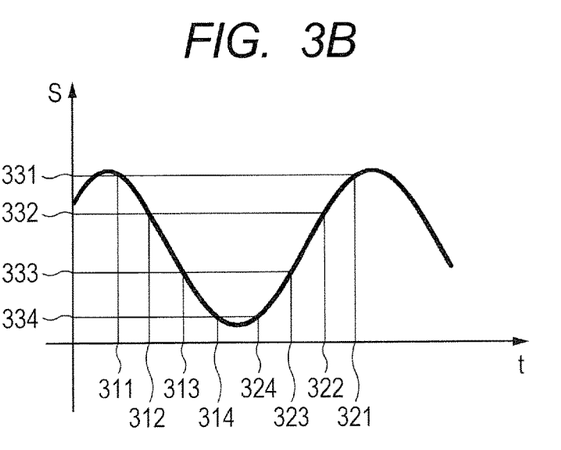

FIG. 3B is a graph for showing how the resonant scanner 206 is driven. In FIG. 3B, the horizontal axis indicates time, and the vertical axis indicates an angle S of oscillation of the resonant scanner 206. A pixel value on a dotted line 301 in FIG. 3A corresponds to a signal obtained at Time 311 or 321 in FIG. 3B. Similarly, pixel values on dotted lines 302, 303, and 304 correspond to signals obtained at Time 312 or 322, Time 313 or 323, and Time 314 or 324, respectively. In this case, Times 311, 312, 313, and 314 are at equal time intervals. Further, Times 321, 322, 323, and 324 are at equal time intervals. The angles of oscillation of the resonant scanner 206 (angles of mirror and angles of resonant scanner) at those times are angles 331, 332, 333, and 334, respectively.

The resonant scanner 206 is not driven at constant speed, and thus, the intervals between the angles 331, 332, 333, and 334 at the respective times are different from each other. In other words, the SLO image illustrated in FIG. 3A is originally distorted in a horizontal direction of a horizontal image. However, the dotted lines 301, 302, 303, and 304 in FIG. 3A need to be displayed at equal intervals in the image. Though described later, in this embodiment, the photodetector 213 is configured to detect a signal as a reference of a scanning position of the measuring light. This detected signal is used to obtain a relationship between the scanning position of the measuring light and time required to perform scanning once with the resonant scanner 206. In this embodiment, intervals between signal acquisitions in obtaining the brightness value are corrected based on the relationship by a method to be described below.

(Description of Angle of Galvano Scanner)

Figure 4:
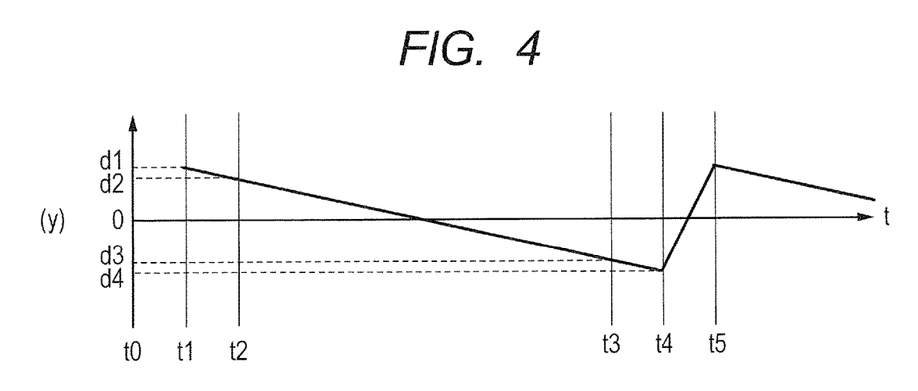
FIG. 4 is an explanatory graph for showing a relationship between an angle of a galvano scanner and a scanning region of measuring light in the first embodiment of the present invention.

In FIG. 4, driving of the galvano scanner 207 is shown.

In FIG. 4, the horizontal axis indicates time, and the vertical axis indicates a rotation angle (y) of the galvano scanner 207. Further, a rotation angle of the galvano scanner 207 that correspond to Time to in FIG. 4 is indicated by an angle dn.

The galvano scanner 207 repeatedly performs operation from Time t1 to Time t5 until a stop signal is transmitted from the control portion 110. Time t0 to Time t1 indicate time required from when a drive signal is output from the control portion 110 to the galvano scanner 207 to when the galvano scanner 207 actually starts being driven. The galvano scanner 207 is driven to rotate from the rotation angle d1 to the rotation angle d4.

In FIG. 4, an effective scan region (angle) of the galvano scanner 207 when scanning the fundus of the eye 200 to be inspected with the measuring light, that is, an SLO image generation region of the fundus of the eye to be inspected is |(rotation angle d2)–(rotation angle d3)|. Therefore, |(rotation angle d1)–(rotation angle d2)| is an acceleration region of the galvano scanner 207, and |(rotation angle d3)–(rotation angle d4)| is a deceleration region of the galvano scanner 207. In particular, the rotation angle d1 is an angle at which the galvano scanner starts being driven. Specifically, an operation of acquiring image data is started at Time t1, and the acquisition of image data to be actually supplied for image generation is started at Time t2. The acquisition of the image data for the image generation is finished at Time t3, and one step of acquiring the image data is ended at Time t4. In this embodiment, the galvano scanner 207 acquires the SLO image data only in forward paths. After finishing acquiring the SLO image data corresponding to one image in the Y direction on the fundus of the eye 200 to be inspected, the galvano scanner 207 is immediately driven from the rotation angle d4 to the rotation angle d1. Then, driving for acquiring SLO image data corresponding to the next one image is started again.

(Description of Drive States of Galvano Scanner, Resonant Scanner, and SLO Light Source)

Next, characteristic operation in this embodiment is described with reference to FIG. 5A and FIG. 5B.

Figure 5A:
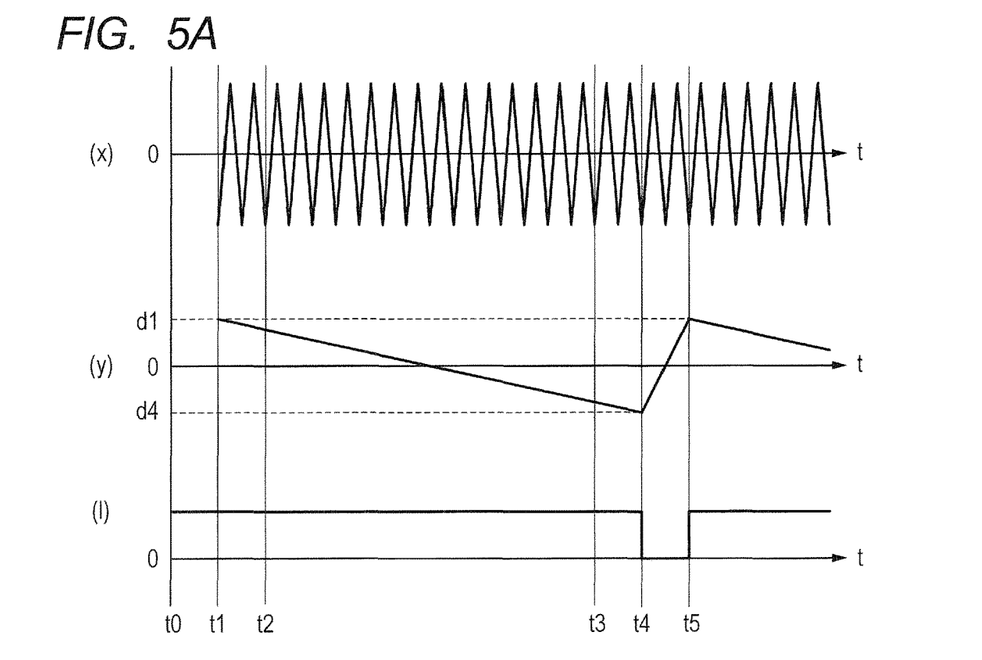
FIG. 5A and FIG. 5B are explanatory graphs for showing relationships among an angle of a resonant scanner, the angle of the galvano scanner, and a state of an SLO light source in the first embodiment of the present invention.
Figure 5B:
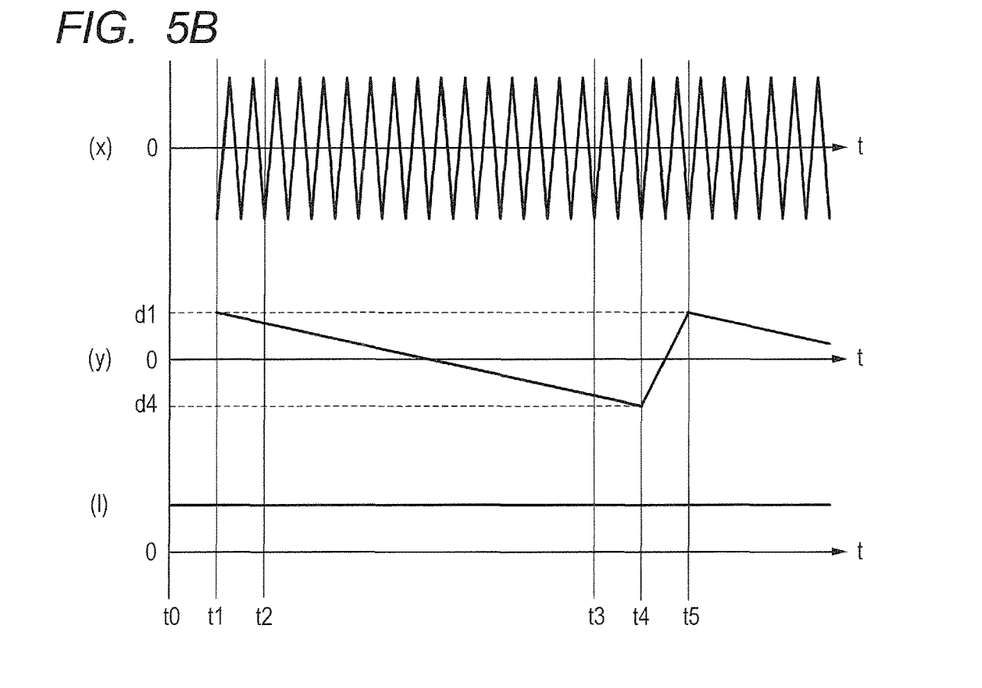

FIG. 5A and FIG. 5B are graphs for showing relationships among an angle of the resonant scanner 206, the angle of the galvano scanner 207, and a drive state of the SLO light source 212. The horizontal axis in each of (x), (y), and (l) of FIG. 5A is Time t. Further, in FIG. 5A, the vertical axis in (x) indicates a displacement (rotation angle) of the resonant scanner 206, and (y) indicates a displacement (rotation angle) of the galvano scanner 207. Further, (l) of FIG. 5A indicates a turned-on state of the SLO light source 212, and more specifically, an amount of the measuring light reflected by the resonant scanner 206 in the direction of the eye to be inspected.

In FIG. 5A, at Time t0, a command to start image acquisition is transmitted from the control portion 110 to the resonant scanner 206, the galvano scanner 207, and the SLO light source 212. In response to the command to start image acquisition, acquisition of an image of the fundus is started from t1. Specifically, the resonant scanner 206 and the galvano scanner 207 start being driven at respective periods. Further, the SLO light source 212 is also turned on.

Now, a relationship between drive of the galvano scanner 207 and turning on of the SLO light source 212 is described.

When the image acquisition is started from Time t1, the galvano scanner 207 travels from the rotation angle d1, which is a scan start angle of the galvano scanner, through the acceleration region, the effective scan region, and the deceleration region, to the rotation angle d4, which is a scan end point angle of the galvano scanner, as described above. The acceleration region is performed from Time t1 to Time t2, the effective scan region is performed from Time t2 to Time t3, and the deceleration region is performed from Time t3 to Time t4. When the galvano scanner 207 is at the rotation angle d1, a start position of the two-dimensional scanning in the region including the fundus for performing the two-dimensional scanning is irradiated with the measuring light. Further, when the galvano scanner 207 is at the rotation angle d4, an end position of the two-dimensional scanning is irradiated with the measuring light. Then, the galvano scanner 207 returns from the rotation angle d4, which is the scan end point angle, back to the rotation angle d1, which is the scan start angle. At that time, as shown in FIG. 5A, in a period from Time t4 to Time t5, which is a timing of returning from the scan end point angle of the galvano scanner to the scan start angle of the galvano scanner, the SLO light source 212 is turned off. In other words, in this embodiment, while the position irradiated with the measuring light is moved from the end position of one cycle of the two-dimensional scanning with the measuring light to the start position of a next cycle of the two-dimensional scanning, irradiation with the measuring light is not intended to generate the two-dimensional image. Therefore, in the segment, the amount of measuring light is reduced to zero. The movement of the position irradiated with the measuring light corresponds to the scanning of the return path with the measuring light using the galvano scanner 207 configured to perform reciprocating scanning for the two-dimensional scanning.

This timing corresponds to a timing when the measuring light traverses in front of the eye to be inspected, which is suppressed not to move by the subject to be inspected by gazing at the fixation lamp with the eye to be inspected, to return back to the start position of the image acquisition. In other words, in a period from the image acquisition in one cycle to the image acquisition in the next cycle, the amount of the measuring light is reduced at the timing when the position irradiated with the measuring light is moved in the predetermined region from which to generate the two-dimensional image of the fundus. The SLO light source 212 is turned off at this timing so that the measuring light does not traverse in the vicinity of the position at which the fixation lamp is presented independently of the acquisition of the image of the fundus. As a result, enhancement of fixation of the eye to be inspected and the reduction in amount of the measuring light radiated to the eye to be inspected are both achieved. The above-mentioned region of the two-dimensional scanning corresponds to the region in which the position irradiated with the measuring light is moved by both scanners, and the region in which the two-dimensional image is generated refers to the region irradiated with the measuring light in the region of the two-dimensional scanning and scanned with the measuring light to obtain brightness information for forming the image.

Figure 6:
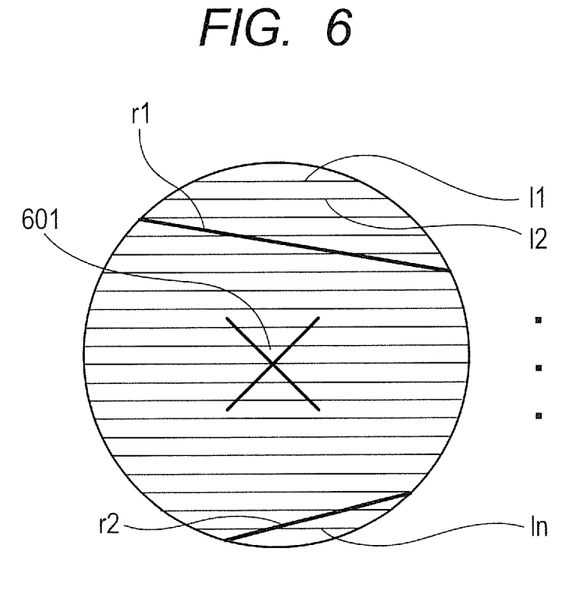
FIG. 6 is an explanatory diagram for illustrating an appearance of an SLO measuring light beam and a fixation lamp as seen from a subject to be inspected in a related-art SLO apparatus.

Now, with reference to FIG. 6 and FIG. 5B, the reason why the improvement in fixation of the eye to be inspected and the reduction in amount of the measuring light radiated to the eye to be inspected may be both achieved is described further in detail.

In FIG. 6, loci of the measuring light and the position at which the internal fixation lamp is lit, which are observed in the SLO apparatus 100 when viewed by the subject to be inspected from the objective lens 201-1 side, are illustrated. In acquiring the image of the fundus, through scanning using the resonant scanner 206 and the galvano scanner 207, the loci of the measuring light are seen as 11, 12, . . . , 1n in FIG.

6 by the subject to be inspected. The optical head 101 includes a lens barrel (not shown), and the eye to be inspected is not irradiated with an SLO light beam vignetted by the lens barrel. Therefore, a region scanned with the SLO light beam generally appears to be a circular region to the subject to be inspected. Further, in the region, the internal fixation lamp is presented as an x shape 601 to the subject to be inspected as illustrated in FIG. 6. The subject to be inspected looks at the center of the x shape 601 to stabilize the fixation.

Here, in the related-art SLO apparatus, when the galvano scanner 207 returns from the scan end point angle to the scan start angle, loci r1 and r2 of the measuring light are observed in the above-mentioned circular region as illustrated in FIG. 6, for example. The measuring light seen when the galvano scanner returns to the scan start angle is different in appearance and number depending on a drive speed of the galvano scanner and a drive speed of the resonant scanner. In FIG. 6, a case where only two loci are observed is illustrated for simplicity.

The driving of the resonant scanner and the galvano scanner, and the turning on of the measuring light source in the related-art SLO apparatus are described using the time axis of FIG. 5B, which is shown in the same manner as FIG. 5A. In FIG. 5B, a time range in which the loci of the measuring light illustrated in FIG. 6 are obtained corresponds to a period from Time t1 to Time t5. The loci r1 and r2 illustrated in FIG. 6 are seen when the galvano scanner 207 returns from the scan end point angle to the scan start angle in a period from Time t4 to Time t5. In other words, the phenomenon occurs because the SLO light source 212 is turned on also in the period from Time t4 to Time t5.

The effective scan region of the galvano scanner 207 in acquiring the brightness information of the eye 200 to be inspected is essentially a region scanned with the measuring light from Time t2 to Time t3. Therefore, lighting of the SLO light source 212 in other regions is unnecessary to the subject to be inspected. As described above, when r1 and r2, which are loci of irregular measuring light, are seen in the field of view in which the loci 11, 12, 13, . . . , 1n of the regular measuring light are seen, attention of the subject to be inspected is distracted by r1 and r2, and the fixation may become unstable.

To address this problem, in this embodiment, as shown in FIG. 5A, in the period from Time t4 to Time t5, which is the timing when the galvano scanner 207 returns from the scan end point angle to the scan start angle, the SLO light source 212 is turned off. Without limitation to the case where the SLO light source 212 is turned off, the amount of light of the SLO light source 212 may be reduced to such an amount as not to disturb the subject to be inspected. With this operation, factors of disturbing the fixation of the eye to be inspected are reduced, and the fixation may be enhanced. Further, according to this embodiment, a comprehensive amount of the measuring light radiated to the subject to be inspected may also be reduced.

In this embodiment, a mode in which the SLO light source 212 is turned off or darkened is exemplified. However, a shutter may be arranged in the optical path of the measuring light, and the shutter may be used to block the measuring light radiated to the eye to be inspected at this timing, for example. Further, in the mode shown in FIG. 5A, the timing to turn on the SLO light source 212 is Time t5, but the SLO light source 212 may be turned on immediately before time corresponding to Time t2 in the next image formation. In this embodiment, in order to secure time for stabilizing the amount of light when the SLO light source spot is turned on, the SLO light source is lit at Time t5. However, when the amount of light of the SLO light source may be stabilized instantly, the SLO light source may be turned on before the galvano scanner 207 enters the effective scan region.

Figure 10:
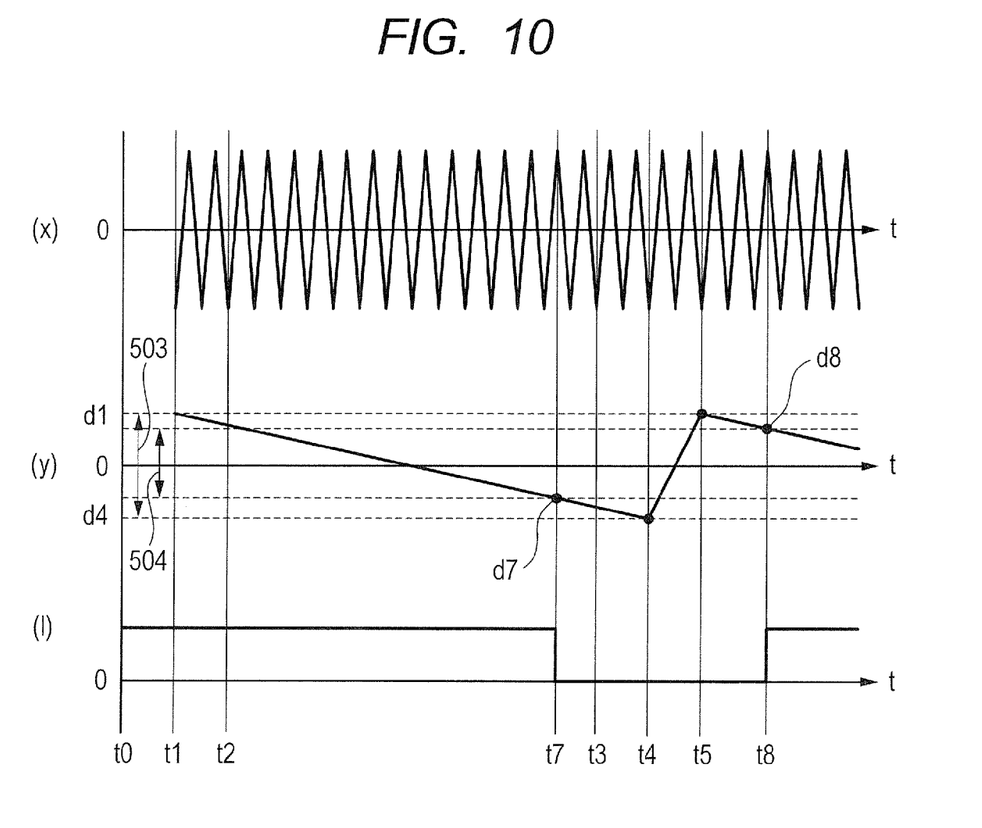
FIG. 10 is an explanatory graph for showing another relationship among an angle of the resonant scanner, an angle of the galvano scanner, and a state of the SLO light source in the first embodiment of the present invention.

Now, a modified example of the timings to turn off and on the SLO light source 212 and the like, which are shown in FIG. 5A, is shown in FIG. 10 in a manner similar to that of FIG. 5A. In the above-mentioned embodiment, the SLO light source 212 is turned off when the rotation angle of the galvano scanner 207 becomes the rotation angle d4, and is turned on when the rotation angle returns to the rotation angle d1.

In contrast, in the modified example shown in FIG. 10, there is assumed a case where a region (length in the y direction) scanned with the measuring light, which corresponds to an angle range in which the galvano scanner 207 is driven, is longer than a diameter of a pupil of the eye 200 to be inspected, for example. In other words, in the assumed case, a drive angle range 503 of the galvano scanner 207 is wider than an angle range 504 corresponding to the scan region on the fundus actually irradiated with the measuring light. At this time, when the rotation angle of the galvano scanner 207 is an angle outside the angle range 504, an outside of the pupil is irradiated with the measuring light, and the measuring light does not reach the fundus of the eye 200 to be inspected. In other words, the eye 200 to be inspected is not irradiated with the measuring light, and hence the irradiation with the measuring light in this angle range is not intended to generate the two-dimensional image. Therefore, in this modified example, in the scanning in the forward path with the measuring light, the SLO light source 212 is turned off or darkened at Time t7 corresponding to a rotation angle d7, at which the measuring light deviates from the angle range 504 in which the eye to be inspected is irradiated with the measuring light. Further, in scanning of the forward path after the measuring light returns from the rotation angle d4 to the rotation angle d1, the SLO light source 212 is turned on or reset to the original amount of light at Time t8 corresponding to a rotation angle d8, at which the rotation angle returns to the angle range 504.

In the example shown in FIG. 10, there has been described a case where a drive angle range is large so that the galvano scanner 207 is rotated until the range scanned with the measuring light exceeds the range of the eye 200 to be inspected irradiated with the measuring light. However, depending on the diameter of the pupil of the eye 200 to be inspected, there is assumed the case where the above-mentioned relationship between the drive angle range 503 in which the eye to be inspected is irradiated with the measuring light and the angle range 504 of the galvano scanner 207 is changed. In such case, depending on the relationship between the drive angle range 503 and the angle range 504 of the galvano scanner 207, the SLO light source 212 may be turned off when the rotation angle of the galvano scanner 207 is the rotation angle d4, and may be turned on at the rotation angle d6 in the scanning of the forward path with the measuring light. Alternatively, the SLO light source 212 may be turned off at the rotation angle d5 of the galvano scanner 207 in the scanning of the forward path with the measuring light, and may be turned on at the rotation angle d1. As described above, the timing of turning on or resetting the amount of light of the SLO light source 212 may be performed, in consideration of time required to stabilize the amount of measuring light, before the above-mentioned timing of turning on or the like by an amount of the time.

In the modified example described above, along with the section scanned with the measuring light without intending to acquire the brightness information of the eye to be inspected, the amount of the measuring light is reduced to zero also in a section scanned with the measuring light in which the brightness information cannot be acquired. As a result, in addition to the effect that the measuring light does not traverse in the vicinity of the position at which the fixation lamp is presented independently of the acquisition of the image of the fundus, the effect of comprehensively reducing time during which the SLO light source 212 is unnecessarily turned on may also be obtained.

(Flow of Acquisition of SLO Image)

Figure 7:
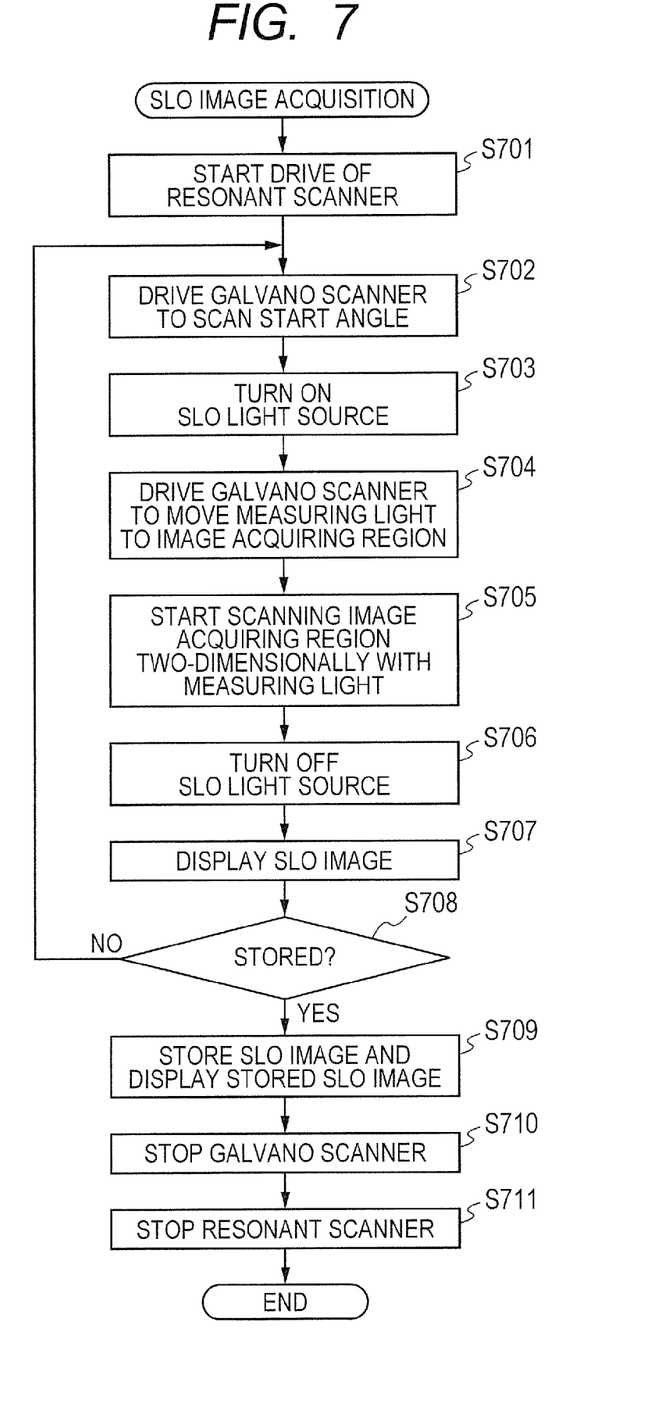
FIG. 7 is a flow chart for illustrating image acquiring steps to acquire an SLO image according to the first embodiment of the present invention.

Next, steps of acquiring an image of the fundus of the eye to be inspected in the SLO apparatus according to this embodiment are described with reference to a flow chart. In FIG. 7, a flow of acquiring an SLO image in this embodiment relating to the method of controlling the SLO apparatus is illustrated. In this image acquisition flow, the SLO light source 212 is turned off, but may be darkened as described above. Specifically, the control portion 110, which is configured to function as a control unit, may control the SLO light source 212 to quench or darken the measuring light. Alternatively, a shutter (not shown) configured to block or darken the measuring light may be arranged to be inserted or removed into or out of the optical path of the measuring light by the control portion 110. More specifically, in the two-dimensional scanning with the measuring light, the amount of the measuring light radiated to the region to be two-dimensionally scanned without intending to generate the fundus image may be controlled to be smaller than the amount of the measuring light radiated to the fundus for generating the fundus image.

In the image acquisition flow in this embodiment, first, in Step S701, the control portion 110 starts drive of the resonant scanner 206. An operation of deflecting the measuring light by the mirror of the resonant scanner 206 is continued until the flow ends. In the subsequent Step S702, the control portion 110 operates the galvano scanner 207 to the scan start angle so that a scan start position of the measuring light may be irradiated with the measuring light. After the operation, in Step S703, the control portion 110 turns on the SLO light source 212.

In Step S704, the control portion 110 drives the galvano scanner 207 to move the position irradiated with the measuring light in a direction of an image acquiring region in the fundus until the position irradiated with the measuring light reaches a two-dimensional scanning start position for acquiring the image of the fundus. Thereafter, in Step S705, the control portion 110 starts scanning the image acquiring region in the fundus two-dimensionally with the measuring light using the resonant scanner 206 and the galvano scanner 207.

After the two-dimensional scanning of the image acquiring region in the fundus with the measuring light in Step S705 is finished, the flow proceeds to Step S706, in which the control portion 110 turns off the SLO light source 212. In Step S707, the control portion 110 generates a fundus image (SLO image) based on a signal obtained with reflected light of the measuring light with which the image acquiring region is two-dimensionally scanned. The generated fundus image is displayed as a so-called preview image on the display portion 112.

An operator observes the fundus image displayed on the display portion 112 to determine whether or not the image is to be stored as a main acquired image to be used for diagnosis and the like, and inputs a result of the determination via the input portion 113 in Step S708. When the input is received from the input portion 113, for example, when an image acquisition button (not shown) is depressed, the control portion 110 determines that the image is to be stored. In this embodiment, the determination in Step S708 is made by the operator, but the determination may be made automatically by setting other criteria. For example, an in-focus state may be determined from a brightness of the fundus image, and when the image is in the in-focus state, it may be determined that the image is to be stored.

When it is determined in Step S708 that the acquired image is to be stored, in Step S709, the control portion 110 stores the fundus image in the storage portion 111, and displays the fundus image again on the display portion 112. Finally, the control portion 110 transmits drive stop signals to the galvano scanner 207 and the resonant scanner 206 to stop the galvano scanner 207 and the resonant scanner 206 in Step S710 and Step S711, respectively. This step completes the acquisition of the image of the fundus by the SLO apparatus 100.

When it is determined in Step S708 that the acquired image is not to be stored, the galvano scanner 207 operates so as to return the position irradiated with the measuring light back to the start position of the two-dimensional scanning. In this embodiment, at this time, the SLO light source 212 has been turned off in Step S706, and hence the eye to be inspected is not irradiated with the measuring light. As described above, this indicates the improvement of the fixation of the eye to be inspected.

During a period in which it is determined in Step S708 that the acquired image is not to be stored, the above-mentioned processing in Step S702 to Step S708 is repeated. While the above-mentioned processing is repeated, the operator may drive the SLO focus lens 210 through input via the input portion 113 to focus the measuring light on the fundus. Alternatively, the control portion 110 may periodically determine the in-focus state and drive the SLO focus lens 210 so that the measuring light is focused on the fundus.

In the above-mentioned embodiment, the case where the SLO light source 212 is turned off while scanning with the measuring light from the end position of one cycle of the two-dimensional scanning to the start position of a next cycle of the two-dimensional scanning has been exemplified. However, in reality, the region two-dimensionally scanned with the measuring light is a region including the fundus of the eye to be inspected and the outer periphery of the fundus. In other words, in reality, in the movement path of the measuring light from the end position of the one cycle of the two-dimensional scanning to the start position of the next cycle of the two-dimensional scanning, a region in which the measuring light is actually observed by the eye to be inspected is only partial. Therefore, the measuring light may be, for example, turned off only when the measuring light traverses the predetermined region from which to acquire the fundus image. Alternatively, the measuring light may be, for example, turned off when a region other than the predetermined region is scanned with the measuring light. In other words, in a state in which the eye to be inspected is irradiated or scanned with the measuring light without intending to generate the two-dimensional image of the fundus of the eye to be inspected, it is only necessary to perform control to turn off the measuring light in the light source, control to block the optical path of the measuring light, and other such control so that at least the fundus is not irradiated with the measuring light. Through the control not to irradiate the fundus with the measuring light as described above, control to reduce the amount of the measuring light radiated to the fundus is performed.

In the first embodiment described above, turning off or reducing the amount of the measuring light is performed in operation of the Y scanner, which is exemplified by the galvano scanner 207, with reference to particular elapsed time from the start of the operation. Specifically, Times t0 to t5 described above, which are timings to change an operation state of the galvano scanner 207, or Times t7 and t8 at which the galvano scanner 207 is at the predetermined rotation angle are used as the reference. However, in the example described above, the measuring light may be turned off or reduced in amount with reference to operation of the resonant scanner 206 that is performed in the X direction in the operation range of the galvano scanner 207.

For example, as described above, in the first portion and the last portion of the rotation of the galvano scanner 207, the operation is not performed at constant speed. In addition, the operation of the galvano scanner 207 is not stabilized. Therefore, it is preferred that the reflected light obtained during the operation be not used for the image generation, and that return light of the measuring light from the eye to be inspected, which is obtained in a state in which the operation of the galvano scanner 207 is stabilized, be used for the image generation. In other words, in scanning in the Y direction of the galvano scanner 207, in at least one of the scanning in the X direction performed first or the scanning in the X direction performed last by the resonant scanner 206, it is preferred to turn off or reduce in amount the measuring light radiated to the fundus. In other words, in the scanning in the X direction, it is preferred to control the amount of the measuring light as in the return path of the scanning in the Y direction using the galvano scanner 207. Alternatively, in a portion in which the scan direction is switched from the forward path to the return path in the reciprocating scanning of the galvano scanner 207, and in a portion in which the scan direction is switched from the return path to the forward path, the above-mentioned unstable operation of the galvano scanner 207 may occur. Therefore, in at least one of the portions in scanning with the measuring light, it is preferred to turn off or reduce in amount the measuring light radiated to the fundus with respect to the scanning with the measuring light in the forward path of the galvano scanner 207.

Second Embodiment

As described above with reference to FIG. 5A and FIG. 5B, the galvano scanner 207 starts operation from the scan start angle, travels through the acceleration region, the effective scan region, and the deceleration region to the scan end angle, and then performs operation to return back to the scan start angle. In the first embodiment described above, there has been described the example in which, during those operations, the SLO light source 212 is turned off or reduced in amount of emitted light to an amount of the measuring light that does not disturb the subject to be inspected to improve the fixation of the eye to be inspected.

In the second embodiment to be described below, with reference to FIG. 8, there is described a case where the galvano scanner 207 starts operation from a scan start position, travels through the acceleration region, the effective scan region, and the scan end angle, and then returns to the scan start angle. In this embodiment, in the course of those operations, the measuring light passes through a light receiving position of the SLO image correcting photodetector 216. At the same time, as in the first embodiment, there is described an example in which the SLO light source 212 is turned off or reduced in amount of light of the SLO light source 212 to an amount of light that does not disturb the subject to be inspected to improve the fixation of the eye to be inspected.

Figure 8:
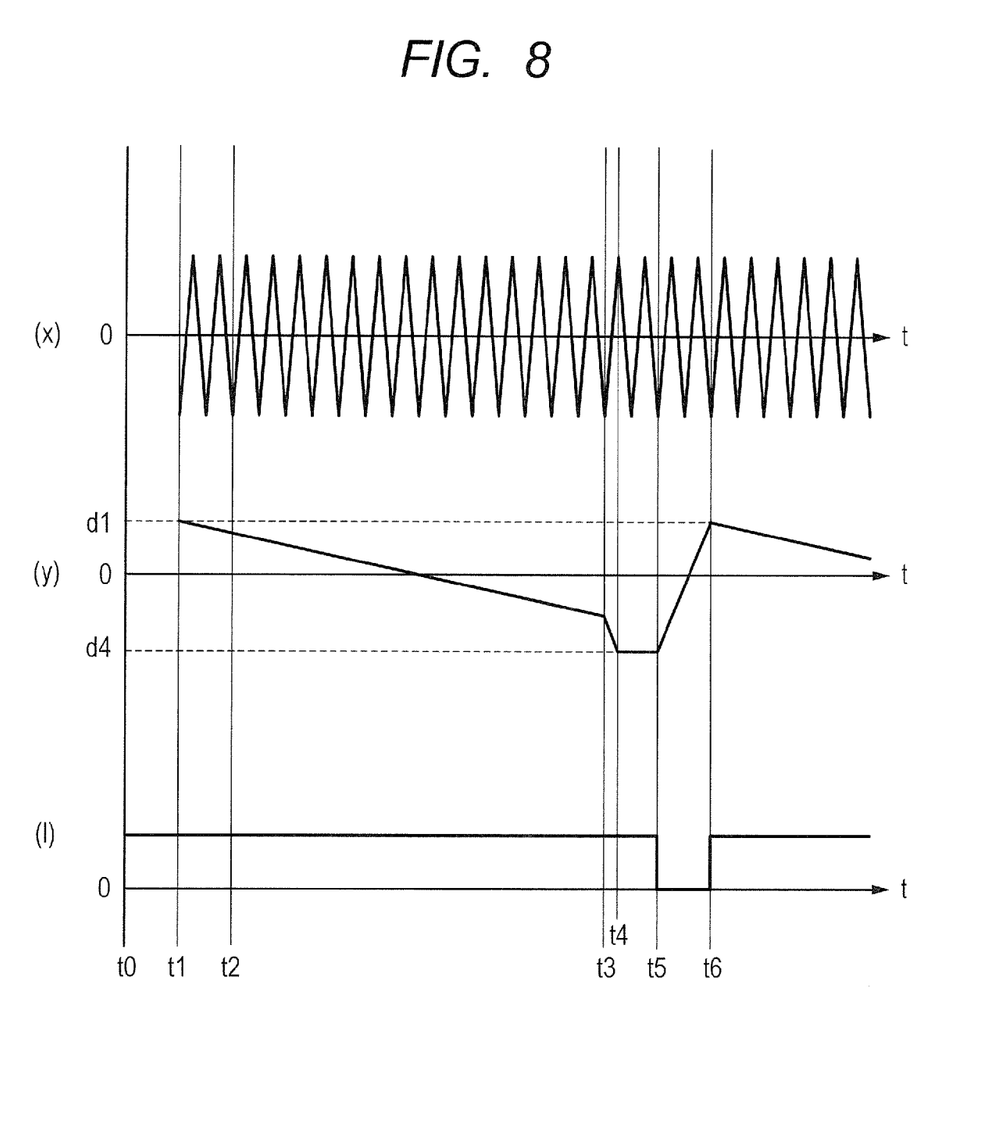
FIG. 8 is an explanatory graph for showing a relationship among an angle of a resonant scanner, an angle of a galvano scanner, and a state of an SLO light source in a second embodiment of the present invention.

FIG. 8 is a graph for showing, in the same manner as FIG. 5A, the scan angle of the resonant scanner 206, the scan angle of the galvano scanner 207, and operation of the SLO light source 212 in the turned-on state after an elapse of time. Further, the horizontal axis and the vertical axis in each of (x), (y), and (l) of FIG. 8 are similar to those of FIG. 5A.

Now, a relationship between the scan angle of the galvano scanner 207 and the turned-on state of the SLO light source 212 is described with reference to FIG. 8.

When the image acquisition is started from Time t1, the galvano scanner 207 starts operation from the rotation angle d1, which is a scan start angle of the galvano scanner, as described above. The galvano scanner 207 travels through the acceleration region and the effective scan region, and moves the position irradiated with the measuring light to the light receiving position of the SLO image correcting photodetector in a period from Time t3 to Time t4. Therefore, in this embodiment, operation of adjusting a scan angle, such as acceleration and deceleration, for moving the position irradiated with the measuring light from the effective scan region to the SLO image correcting photodetector is performed. Then, the galvano scanner travels through the angle corresponding to the region scanned with the measuring light, which is the light receiving position, in a period from Time t4 to Time t5 to return back to the scan start angle of the galvano scanner. Further, in a period from Time t5 to Time t6, which is a timing at which the galvano scanner 207 returns to the scan start angle of the galvano scanner, the control portion 110 turns off the SLO light source 212. As in the first embodiment, the SLO light source 212 is turned off at this timing to improve the fixation of the eye to be inspected.

In the first embodiment, the galvano scanner 207 returns directly to the scan start angle after scanning the deceleration region. In contrast, in the second embodiment, after passing through the effective scan region, the galvano scanner 207 returns to the scan start angle after operating to pass through the position at which the SLO image correcting photodetector 216 is scanned with the measuring light.

In general, the resonant scanner is not driven with constant speed in a range of operating angles as described above with reference to FIG. 3A and FIG. 3B. Therefore, in order to generate a better SLO image, it is preferred to correct a relationship between time and the position irradiated with the measuring light. In this embodiment, information from the SLO image correcting photodetector 216 is used to correct the intervals between signal acquisitions by the photodetector 213. This correction may be performed to correct a position from which to acquire a signal on the fundus in a direction of scanning with the measuring light using the resonant scanner, to thereby generate an SLO image in which an image distortion is suppressed. In order to perform the correction with higher accuracy, the SLO image correcting photodetector 216 may be scanned with the measuring light a plurality of times.

(Description of Photodetector)

Now, the SLO image correcting photodetector 216 is described with reference to FIG. 2.

In order to correct the SLO image, the angle of the mirror of the galvano scanner 207 is changed so that the position irradiated with the measuring light passes through the light receiving portion of the SLO image correcting photodetector 216. The change in angle of the mirror may be controlled to irradiate with the measuring light the SLO image correcting photodetector 216, which is arranged off the axis of the measuring light of the SLO apparatus 100. The SLO image correcting photodetector 216 is arranged off the optical axis of the measuring light when the measuring light enters the eye to be inspected. In other words, the SLO image correcting photodetector 216 forms a light receiving element, which is arranged in a region that is not intended to generate the fundus image in the region two-dimensionally scanned with the measuring light, and is configured to receive the measuring light. The light receiving element is configured to output a signal for correcting an image distortion, which is used in generating the fundus image.

A shape of a waveform and a pulse width of an analog signal detected by the photodetector 213 are changed depending on a position of the SLO focus lens 210. Therefore, a detection time needs to be calculated based on a center of gravity of the waveform of the analog signal, a center of the pulse width of the analog signal, or the like without depending on the position of the SLO focus lens 210. When the analog signal has hysteresis by being binarized, the center may be calculated depending on the degree of the hysteresis. The detection time may be calculated using a special calculation expression depending on the output characteristics of the photodetector and the drive characteristics of the resonant scanner. In order to detect the detection time more accurately, two or more photodetectors may be arranged.

(Flow of SLO Image Acquisition)

Figure 9:
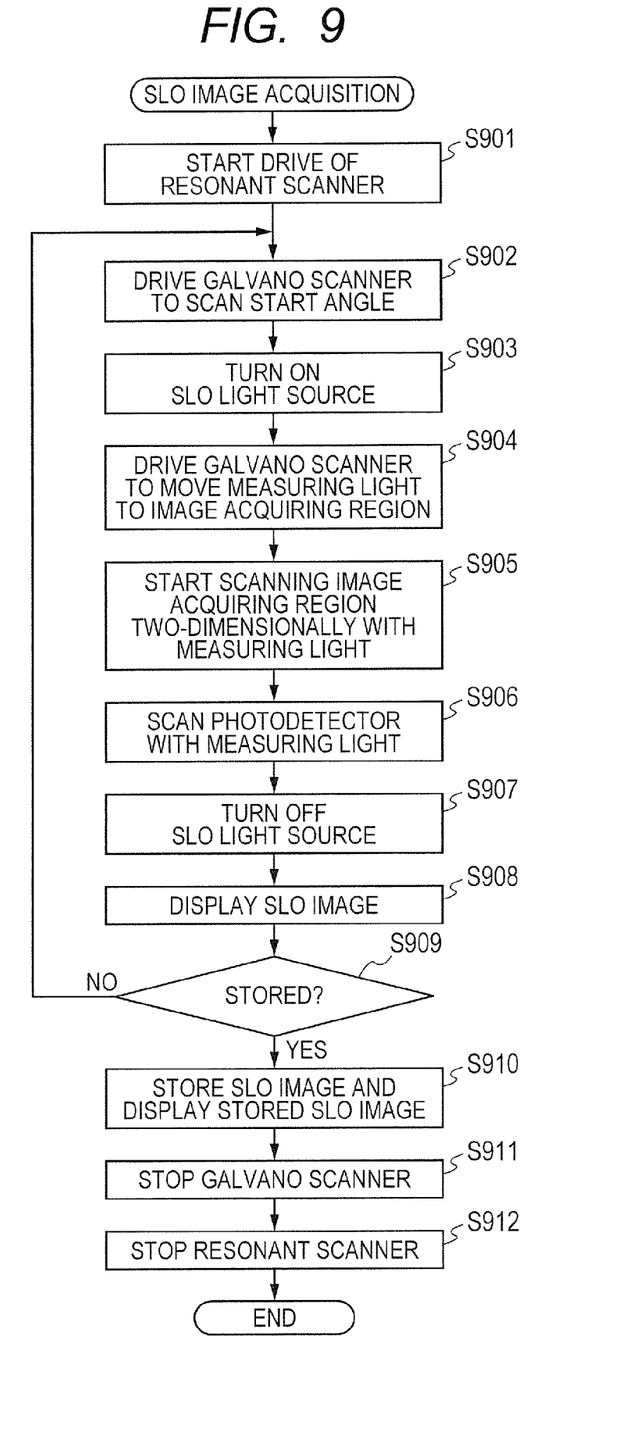
FIG. 9 is a flow chart for illustrating image acquiring steps to acquire an SLO image according to the second embodiment of the present invention.

Next, steps of acquiring an image of the fundus of the eye to be inspected in the SLO apparatus according to the second embodiment are described with reference to a flow chart. In FIG. 9, a flow of acquiring an SLO image in this embodiment is illustrated. The flow chart illustrated in FIG. 9 is different from the flow chart illustrated in FIG. 7 in that control in which the measuring light passes through the SLO image correcting photodetector 216 is included after the two-dimensional scanning of the fundus with the measuring light is finished.

In the image acquisition flow in this embodiment, first, in Step S901, the control portion 110 starts drive of the resonant scanner 206. In the subsequent Step S902, the control portion 110 operates the galvano scanner 207 to the scan start angle so that a scan start position of the measuring light may be irradiated with the measuring light. After the operation, in Step S903, the control portion 110 turns on the SLO light source 212.

In Step S904, the control portion 110 drives the galvano scanner 207 to move the position irradiated with the measuring light in a direction of an image acquiring region in the fundus until the position irradiated with the measuring light reaches a two-dimensional scanning start position for acquiring the image of the fundus. Thereafter, in Step S905, the control portion 110 starts scanning the image acquiring region in the fundus two-dimensionally with the measuring light using the resonant scanner 206 and the galvano scanner 207.

In this embodiment, the image is generated using the signal information obtained by the photodetector 213. After the two-dimensional scanning of the predetermined image acquiring region of the fundus with the measuring light in Step S905, in Step S906, the galvano scanner 207 is operated so that the SLO image correcting photodetector 216 is irradiated with the measuring light. At this time, an optical axis along which the measuring light reaches the SLO image correcting photodetector 216 is different from an optical axis along which the measuring light reaches the eye to be inspected, and hence the measuring light does not enter the eye to be inspected. The SLO image correcting photodetector 216 is arranged at a position at which the measuring light enters when the mirror of the resonant scanner 206 has a predetermined angle, for example. Therefore, when a relationship between a timing of the entering and a scanning position of the measuring light, which corresponds to a rotation angle of the mirror at that time, has been obtained in advance, the scanning of the fundus with the measuring light using the resonant scanner 206 may be known from the timing of the entering.

After the position signal is acquired by the SLO image correcting photodetector 216 in Step S906, the flow proceeds to Step S907, in which the control portion 110 turns off the SLO light source 212. In Step S908, the control portion 110 generates a fundus image (SLO image) based on a signal obtained by reflected light of the measuring light with which the two-dimensional scanning has been performed, and the position signal obtained by the SLO image correcting photodetector 216. The generated fundus image is displayed on the display portion 112 as a so-called preview image.

An operator observes the fundus image displayed on the display portion 112 to determine whether or not the image is to be stored as a main acquired image to be used for diagnosis and the like, and inputs a result of the determination via the input portion 113 in Step S909. When the input is received from the input portion 113, for example, when an image acquisition button (not shown) is depressed, the control portion 110 determines that the image is to be stored. In this embodiment, the determination in Step S909 is made by the operator, but the determination may be made automatically by setting other criteria. For example, an in-focus state may be determined from a brightness of the fundus image, and when the image is in the in-focus state, it may be determined that the image is to be stored.

When it is determined in Step S909 that the acquired image is to be stored, in Step S910, the control portion 110 stores the fundus image in the storage portion 111, and displays the fundus image again on the display portion 112. Finally, the control portion 110 transmits drive stop signals to the galvano scanner 207 and the resonant scanner 206 to stop the galvano scanner 207 and the resonant scanner 206 in Step S911 and Step S912, respectively. This step completes the acquisition of the image of the fundus by the SLO apparatus 100.

When it is determined in Step S909 that the acquired image is not to be stored, the galvano scanner 207 operates so as to return the position irradiated with the measuring light back to the start position of the two-dimensional scanning. In this embodiment, at this time, the SLO light source 212 has been turned off in Step S907, and hence the eye to be inspected is not irradiated with the measuring light. As described above, this indicates the improvement of the fixation of the eye to be inspected.

During a period in which it is determined in Step S909 that the acquired image is not to be stored, the above-mentioned processing in Step S902 to Step S909 is repeated. While the above-mentioned processing is repeated, the operator may drive the SLO focus lens 210 through input via the input portion 113 to focus the measuring light on the fundus. Alternatively, the control portion 110 may periodically determine the in-focus state and drive the SLO focus lens 210 so that the measuring light is focused on the fundus.

Other Embodiments

A scanning laser ophthalmoscope (SLO apparatus) is given as an example of an ophthalmologic image acquiring apparatus as described above. However, the present invention may generally apply to an OCT apparatus.

In such case, a third dichroic mirror (not shown) which is an example of an optical path branching element is preferable provided between the first dichroic mirror 205 and the lens 201-2 on the optical path L2 in FIG. 2, so as to provide an OCT optical system on an reflected optical path of the third dichroic mirror. A light source of the OCT optical apparatus may emits a light having a wavelength band including 1 μm. By using that light, a bright line caused by scanning the fundus with the light emitted from the OCT light source becomes harder to see by the person to be inspected, in comparison with a bright line generated by the light emitted from the OCT light source, the light being in a wavelength band including 800 nm.

On the other hand, a bright line caused by scanning the light from the SLO light source 212 which emits the light having a wavelength near the visible wavelength band is brighter than the bright line caused by the light from the OCT light source, and therefore it becomes difficult to stabilize the fixation state of the eye to be inspected. Hence, in the scanning (a return path of the sub scanning direction) the fundus with the measuring light without intending to generate the two-dimensional image (SLO image), an amount of the measuring light radiated on the fundus is controlled to smaller (turn-off the SLO light source) to decrease an useless movement of the eye to be inspected.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-027769, filed Feb. 17, 2016 and Japanese Patent Application No. 2016-232938, filed Nov. 30, 2016 which are hereby incorporated by reference herein in their entirety.

What is claimed is:

1. An ophthalmologic apparatus comprising:
a scan unit configured to repeat two-dimensional scanning on a fundus of an eye to be inspected with measuring light, the two-dimensional scanning including scanning in a first direction and scanning in a second direction, wherein the second direction is different from the first direction, and wherein a speed of reciprocating scanning in the second direction is lower than that in the first direction;
an image generation unit configured to generate a two-dimensional image of the fundus based on reflected light of the measuring light from the fundus that is two-dimensionally scanned; and
a control unit configured to control, in the two-dimensional scanning, an amount of the measuring light that is radiated to the fundus in scanning not being used to generate the two-dimensional image including at least scanning of a return path in the second direction to be smaller than an amount of the measuring light that is radiated to the fundus in scanning being used to generate the two-dimensional image.

2. An ophthalmologic apparatus according to claim 1, wherein the irradiation with the measuring light not being used to generate the two-dimensional image at least includes irradiation in moving, from an end position of one cycle of the two-dimensional scanning to a start position of a next cycle of the two-dimensional scanning, a position irradiated with the measuring light across the fundus.

3. An ophthalmologic apparatus according to claim 1, wherein the scan unit comprises:
(a) an X scanner configured to perform reciprocal scanning with the measuring light in the first direction; and
(b) a Y scanner configured to perform reciprocal scanning with the measuring light at least in the second direction, at a speed lower than a speed of the reciprocating scanning of the X scanner, and
wherein the irradiation with the measuring light not being used to generate the two-dimensional image at least includes irradiation in scanning with the measuring light in a return path of the scanning by the Y scanner.

4. An ophthalmologic apparatus according to claim 3, wherein the control unit is configured to set an amount of the measuring light in at least one of first reciprocating scanning or last reciprocating scanning by the X scanner in the second direction to be smaller than the amount of the measuring light that is radiated to the fundus and is used to generate the two-dimensional image.

5. An ophthalmologic apparatus according to claim 3, wherein the X scanner comprises a resonant scanner, and the Y scanner comprises a galvano scanner.

6. An ophthalmologic apparatus according to claim 1, further comprising a light receiving element, which is arranged outside a scanning region of the measuring light on the fundus, and inside a region two-dimensionally scanned with the measuring light,
wherein the light receiving element is configured to output a signal for correcting an image distortion, which is used in generating the two-dimensional image.

7. An ophthalmologic apparatus according to claim 6, wherein the control unit is configured to control an amount of the measuring light during a period from irradiating the light receiving element with the measuring light to returning to a start position of the two-dimensional scanning to be smaller than the amount of the measuring light that is radiated to the fundus and is used to generate the two-dimensional image.

8. An ophthalmologic apparatus according to claim 1, further comprising a fixation lamp configured to emit a fixation light radiated on the fundus through the scan unit,
wherein the control unit is configured to perform such control that the fixation lamp turns on or off in conjunction with the scanning with the measuring light by the scan unit, and to perform such control that the fundus is not irradiated with the measuring light, to thereby control an amount of the measuring light radiated to the fundus to be smaller.

9. An ophthalmologic apparatus comprising:
a scan unit configured to repeatedly perform two-dimensional scanning on a fundus of an eye to be inspected with measuring light, the two-dimensional scanning including scanning in a first direction and scanning in a second direction, wherein the second direction is different from the first direction, and wherein a speed of reciprocating scanning in the second direction is lower than that in the first direction;
an image generation unit configured to generate a two-dimensional image of the fundus based on reflected light of the measuring light from the fundus that is two-dimensionally scanned; and
a control unit configured to control an amount of the measuring light radiated to the fundus in scanning of a return path in the second direction to be smaller than an amount of the measuring light radiated to the fundus in scanning of a forward path in the second direction.

10. An ophthalmologic apparatus according to claim 9, wherein the control unit is configured to control an amount of the measuring light used to scan at least one of a portion of switching from the forward path to the return path or a portion of switching from the return path to the forward path in the scanning with the measuring light in the second direction to be smaller than the amount of the measuring light radiated to the fundus in the forward path.

11. An ophthalmologic apparatus according to claim 9, wherein the control unit is configured to control, in the controlling of the amount of the measuring light to be smaller, a light source configured to emit the measuring light to quench or darken the measuring light.

12. An ophthalmologic apparatus according to claim 9, wherein the control unit is configured to insert or remove, in the controlling of the amount of the measuring light to be smaller, a shutter configured to block or darken the measuring light into or out of an optical path of the measuring light.

13. An ophthalmologic apparatus according to claim 9, further comprising a fixation lamp configured to emit a fixation light radiated on the fundus through the scan unit,
wherein the control unit is configured to perform such control that the fixation lamp turns on or off in conjunction with the scanning with the measuring light by the scan unit, and to perform such control that the fundus is not irradiated with the measuring light, to thereby control an amount of the measuring light radiated to the fundus to be smaller.

14. An ophthalmologic apparatus according to claim 9, further comprising:
an OCT optical system;
an optical path branching element configured to branch an optical path of the OCT optical system from an optical path on which the scan unit is located; and
a wavelength-sweeping light source which is located on the OCT optical system, configured to emit a light in a wavelength band including 1 µm.

15. A method of controlling an ophthalmologic apparatus, the method comprising:
repeatedly performing, by a scan unit, two-dimensional scanning on a fundus of an eye to be inspected with measuring light, the two-dimensional scanning including scanning in a first direction and scanning in a second direction, wherein the second direction is different from the first direction, and wherein a speed of reciprocating scanning in the second direction is lower than that in the first direction;
generating a two-dimensional image of the fundus based on reflected light of the measuring light from the fundus that is two-dimensionally scanned; and
controlling, in the two-dimensional scanning, an amount of the measuring light that is radiated to the fundus in scanning not being used to generate the two-dimensional image including at least scanning of a return path in the second direction to be smaller than an amount of the measuring light that is radiated to the fundus in scanning being used to generate the two-dimensional image.

16. A method of controlling an ophthalmologic apparatus according to claim 15, wherein the controlling comprises controlling the amount of the measuring light radiated to the fundus to be smaller by performing control so that the fundus is not irradiated with the measuring light.

17. A non-transitory computer-readable storage medium storing a program for causing a computer to execute the method according to claim 15.

18. A method of controlling an ophthalmologic apparatus, the method comprising:
repeatedly performing, by a scan unit, on a fundus of an eye to be inspected, two-dimensional scanning with measuring light, the two-dimensional scanning including scanning in a first direction and scanning in a second direction, wherein the second direction is different from the first direction, and wherein a speed of reciprocating scanning in the second direction is lower than that in the first direction;
generating a two-dimensional image of the fundus based on reflected light of the measuring light from the fundus that is two-dimensionally scanned; and
controlling an amount of the measuring light radiated to the fundus in scanning of a return path in the second direction to be smaller than an amount of the measuring light radiated to the fundus in scanning of a forward path in the second direction.

19. A method of controlling an ophthalmologic apparatus according to claim 18, wherein the controlling comprises controlling the amount of the measuring light radiated to the fundus to be smaller by performing control so that the fundus is not irradiated with the measuring light.

20. A non-transitory computer-readable storage medium storing a program for causing a computer to execute the method according to claim 18.

* * * * *